(12) United States Patent
Neumann (10) Patent No.: US 11,861,468 B2
(45) Date of Patent: Jan. 2, 2024

(54) METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE

(71) Applicant: KPN Innovations, LLC, Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 5 days.

(21) Appl. No.: 16/886,647

(22) Filed: May 28, 2020

(65) Prior Publication Data
US 2021/0375406 A1    Dec. 2, 2021

(51) Int. Cl.
*G06N 20/00*    (2019.01)
*G16H 10/40*    (2018.01)
(Continued)

(52) U.S. Cl.
CPC .......... *G06N 20/00* (2019.01); *G06F 18/214* (2023.01); *G06N 20/20* (2019.01); *G16H 10/40* (2018.01); *G16H 50/30* (2018.01)

(58) Field of Classification Search
CPC ........ G16H 10/40; G16H 50/30; G16H 10/60; G06N 20/20; G06K 9/6256
See application file for complete search history.

(56) References Cited

U.S. PATENT DOCUMENTS 8,000,982 B2    8/2011    Kane et al.
8,655,817 B2 *    2/2014    Hasey ................ G16H 50/30
                                                                706/45
(Continued)

FOREIGN PATENT DOCUMENTS

CN    103984847 A    8/2014
RU       2689423 C1    5/2019
WO    WO2018031991   2/2018

OTHER PUBLICATIONS

R.L. Prosst et al., "Methylene Blue in the Evaluation of Gastrointestinal Tract Integrity: Potential Limitations", 2005, pp. 246-249 (Year: 2005).*

(Continued)

*Primary Examiner* — Rajesh Khattar
*Assistant Examiner* — Steven G. S. Sanghera
(74) *Attorney, Agent, or Firm* — Caldwell Intellectual Property Law (57) ABSTRACT

A system for determining a plurality of biological outcomes using a plurality of dimensions of biological extraction user data and artificial intelligence, the system including a computing device configured to receive, a plurality of dimensions of biological extraction data, generate, a first machine learning process comprising a plurality of biosektch measurements wherein the first machine learning process is trained as a function of training data to output a dimensional history of a user as a function of biological extraction data, output as a function of the plurality of dimensions of biological extraction data and the first machine learning process, the dimensional history of the user; and determine, using a second machine learning process and the dimensional history of the user, at least a biological outcome associated with the user.

16 Claims, 4 Drawing Sheets

(51) Int. Cl.
  *G06N 20/20* (2019.01)
  *G16H 50/30* (2018.01)
  *G06F 18/214* (2023.01)

(56) References Cited

U.S. PATENT DOCUMENTS

| | | | |
|---|---|---|---|
| 8,762,167 B2 | 6/2014 | Blander et al. | |
| 10,282,512 B2* | 5/2019 | Bennett | G16H 50/00 |
| 10,553,319 B1* | 2/2020 | Neumann | G16H 50/20 |
| 2010/0017388 A1* | 1/2010 | Glover | G06F 16/9535 |
| | | | 707/E17.001 |
| 2013/0151270 A1 | 6/2013 | Nova et al. | |
| 2014/0088996 A1 | 3/2014 | Daman | |
| 2014/0108044 A1* | 4/2014 | Reddy | G16H 15/00 |
| | | | 705/3 |
| 2014/0324459 A1* | 10/2014 | Barfield | G16H 10/60 |
| | | | 705/3 |
| 2015/0046465 A1* | 2/2015 | Lambert | G01N 33/50 |
| | | | 707/741 |
| 2016/0007899 A1* | 1/2016 | Durkee | G09B 23/28 |
| | | | 600/300 |
| 2017/0053082 A1* | 2/2017 | Pereira | G16H 50/20 |
| 2017/0109499 A1* | 4/2017 | Doshi | H04L 63/0428 |
| 2018/0068083 A1* | 3/2018 | Cohen | G16H 10/60 |
| 2018/0240542 A1 | 8/2018 | Grimmer et al. | |
| 2019/0362648 A1* | 11/2019 | Hadjigeorgiou | G16H 20/60 |
| 2020/0270699 A1* | 8/2020 | Mir | C12Q 1/6883 |
| 2021/0158909 A1* | 5/2021 | Ng | G16H 20/00 |
| 2021/0166803 A1* | 6/2021 | Ellis | G06N 20/00 |

OTHER PUBLICATIONS

Genopalate.
https://www.ncbi.nlm.nih.gov/pmc/articles/PMC5224962/pdf/1890e40.pdf retrieved on Jul. 10, 2019.

* cited by examiner

METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE

FIELD OF THE INVENTION

The present invention generally relates to the field of artificial intelligence. In particular, the present invention is directed to methods and systems for determining a plurality of biological outcomes using a plurality of dimensions of biological extraction user data and artificial intelligence.

BACKGROUND

Design of systems for analysis of biological data is often complicated by the extreme complexity and variability of the subject matter between subjects. A vast multiplicity of factors to be considered is further complicated by a complex array of subtle, but crucial data. Worse still, a given factor may vary significantly between subjects, and in ways that can frustrate consistent application of biological data to analytical techniques.

SUMMARY OF THE DISCLOSURE

In an aspect, a system for determining a plurality of biological outcomes using a plurality of dimensions of biological extraction user data and artificial intelligence, the system comprising a computing device, wherein the computing device is designed and configured to receive a plurality of dimensions of biological extraction data; generate a first machine learning process comprising a plurality of biosketch measurements where the first machine learning process is trained as a function of training data to output a dimensional history of a user as a function of biological extraction data; output as a function of the plurality of dimensions of biological extraction data and the first machine learning process, the dimensional history of the user, and determine, using a second machine learning process and the dimensional history of the user, at least a biological outcome associated with the user.

In an aspect, a method of determining a plurality of biological outcomes using a plurality of dimensions of biological extraction user data and artificial intelligence, the method comprising receiving by at least a computing device, a plurality of dimensions of biological extraction data; generating by the at least a computing device, a first machine learning process comprising a plurality of biosketch measurements wherein the first machine learning process is trained as a function of training data to output a dimensional history of a user as a function of biological extraction data; outputting as a function of the plurality of dimensions of biological extraction data and the first machine learning process, the dimensional history of the user; and determining by the at least a computing device, using a second machine learning process and the dimensional history of the user, at least a biological outcome associated with the user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a system and method for determining a plurality of biological outcomes using a plurality of dimensions of biological extraction user data and artificial intelligence. In non-limiting embodiments described herein, artificial intelligence may refer to a machine learning process, as described in further detail below. In non-limiting embodiments, system may receive plurality of dimensions of biological extraction, as defined below. In non-limiting embodiments, generating a dimensional history of a user may use plurality of dimensions of biological extraction data, as described in further detail below. Dimensional history data may be used as an input to at least a first machine learning algorithm to train a model to determine a plurality of correlated biosketch measurements of a user. A second machine learning process may be trained with a variety of available resources to determine the accuracy of user-reported plurality of dimensions of biological extraction data. Dimensional history data may be input into a machine learning process including a model trained with this data to determine a biological outcome of a user.

Figure 1:
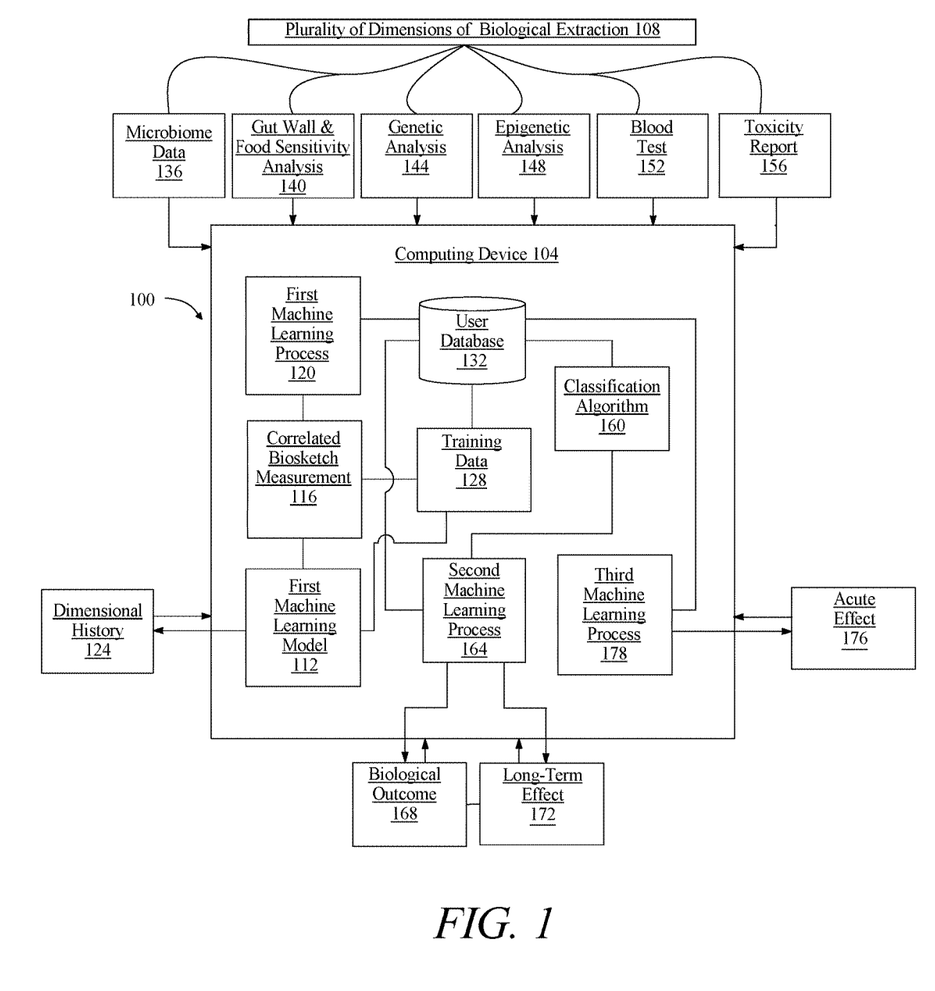
FIG. 1 is a block diagram of an exemplary embodiment of a system for determining a plurality of biological outcomes using a plurality of dimensions of biological extraction user data and artificial intelligence.

Referring now to FIG. 1, an exemplary embodiment of a system 100 for determining biological outcomes using artificial intelligence is illustrated. System 100 includes at least a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently, or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory between computing devices 104. Computing device 104 may be implemented using a "shared nothing" architecture in which data is cached at the worker, in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may be designed and configured to receive plurality of dimensions of biological extraction 108. A "dimension of biological extraction," as used in this disclosure may refer to a measurement corresponding to a category of biological extraction data including without limitation microbiome analysis, genetic analysis, epigenetic analysis, blood test, gut wall and food sensitivity analysis, and/or toxicity report, including for instance, and without limitation, as described in U.S. Nonprovisional application Ser. No. 16/530,329 filed on Aug. 2, 2019, and entitled "METHODS AND SYSTEMS FOR GENERATING COMPATIBLE SUBSTANCE INSTRUCTION SETS USING ARTIFICIAL INTELLIGENCE," the entirety of which is incorporated herein by reference. As a non-limiting example, a plurality of dimensions of biological extraction 108 may refer to at least two of six categories of biological extraction, as described in further detail below.

Still referring to FIG. 1, at least a computing device 104 may generate, using the plurality of dimensions of biological extraction 108 data and a first machine learning model 112, correlating dimensional history 124 of the user. First machine learning model 112 contains a plurality of correlated biosketch measurements 116 generated by a first machine learning process 120. First machine learning process may include generating first machine learning model 112 as described below in more detail. A "dimensional history," as used in this description, is a body of data describing a relationship containing at least two elements of data, including at least an element of the plurality of dimensions of biological extraction 108 data and at least an output of a correlated biosketch measurement 116. A "correlated biosketch measurement," as used in this disclosure, is a mathematical, heuristic, causative, correlated, proportional, and/or any other relationship between at least two elements of data of the plurality of dimensions of biological extraction 108 data. A correlated biosketch measurements 116 may be, without limitation, a matrix and/or vector, describing values, coefficients, variables, or the like, that describe at least a relationship between at least two of more elements of data of the plurality of dimensions of biological extraction 108. In non-limiting illustrative examples, this may include two elements of data within the same category of data, such as two elements of genetic analysis, and/or two elements of data in disparate categories, such as genetic analysis and toxicity report. A first machine learning process 120, as described herein, generate a plurality of correlated biosketch measurements. In non-limiting illustration examples, correlated biosketch measurements 116 may describe a food sensitivity as a function of the presence and number of active cultures of a strain of bacteria in a user's gut. A machine learning model may be trained with at least a correlated biosketch measurements 116 and may be used as an input into a machine learning process to generate a dimensional history 124 of a user. A dimensional history 124 may be generated by a machine learning model containing at least a correlated biosketch measurements 116 using at least an element of a plurality of dimensions of biological extraction 108 data. In non-limiting illustrative examples, elements of data of a plurality of dimensions of biological extraction 108 data may be further narrowed into subsets by use of a classifier, as described below.

Still referring to FIG. 1, first machine learning model may use at least a supervised machine learning algorithm. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include an element of biological extraction 108 data as described above as inputs, dimensional history 124 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

Supervised machine learning process may include classification algorithms, defined as processes whereby at least a computing device 104 derives, from training data, a model for sorting inputs into categories or bins of data. Classification may be performed using, without limitation, linear classifiers such as without limitation logistic regression and/or naive Bayes classifiers, regression algorithms, nearest neighbor classifiers, support vector machines, decision trees, boosted trees, random forest classifiers, and/or neural network-based classifiers, such as supervised neural net algorithms. Supervised machine learning process may include, without limitation, machine learning processes as described in U.S. Nonprovisional application Ser. No. 16/520,835, filed on Jul. 3, 2019, and entitled "METHODS AND SYSTEMS FOR ACHIEVING VIBRANT CONSTITUTION BASED ON USER INPUTS," the entirety of which is incorporated herein by reference.

Still referring to FIG. 1, computing device 104 may select at least a first machine learning process 120, as described before, with the at least a plurality of dimensions of biological extraction 108 data as an input to generate a correlated biosketch measurements 116 as an output. Correlated biosketch measurements 116 may be used as training data to train a model for generating a dimensional history 124. A machine learning model for generating a dimensional history 124 output may be trained with at least a first correlated biosketch measurements 116 input. Machine learning model may be trained by training data 128 retrieved from a user database 132, as described in further detail below. First machine learning model may accomplish this by using training data 128 containing a plurality of dimensions of biological extraction 108 and a correlated biosketch measurement 116 as it relates to other users and/or sets of data, such as by use of a classifier, as described in further detail below.

Continuing in reference to FIG. 1, "training data," as used herein, is data containing correlations that a first machine learning model may use to model relationships between two or more categories of data elements. For instance, and without limitation, training data 128 may include a plurality of data entries, each entry representing a set of data elements that were recorded, received, and/or generated together; data elements may be correlated by shared existence in a given data entry, by proximity in a given data entry, or the like. Multiple data entries in training data 128 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 128 according to various correlations; correlations may indicate causative and/or predictive links between categories of data elements, which may be modeled as relationships such as mathematical relationships by machine learning processes as described in further detail below. Training data 128 may be formatted and/or organized by categories of data elements, for instance by associating data elements with one or more descriptors corresponding to categories of data elements. As a non-limiting example, training data 128 may include data entered in standardized forms by persons or processes, such that entry of a given data element in a given field in a form may be mapped to one or more descriptors of categories. Elements in training data 128 may be linked to descriptors of categories by tags, tokens, or other data elements; for instance, and without limitation, training data 128 may be provided in fixed-length formats, formats linking positions of data to categories such as comma-separated value (CSV) formats and/or self-describing formats such as extensible markup language (XML), enabling processes or devices to detect categories of data.

Alternatively or additionally, training data 128 may include one or more elements that are not categorized; that is, training data 128 may not be formatted or contain descriptors for some elements of data. Machine learning algorithms and/or other processes may sort training data 128 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 128 to be made applicable for two or more distinct machine learning algorithms as described in further detail below. Training data 128 used by computing device 104 may correlate any input data as described in this disclosure to any output data as described in this disclosure. As a non-limiting illustrative example, at least an element of biological extraction 108 data and biosketch measurements may be used with invention.

Referring now to FIG. 1, plurality of dimensions of biological extraction 108 data of a user may include microbiome data 136 including microbiome analysis that comes from a user stool sample. Analysis of user stool sample may come from database, medical professional, and/or user input. As described here, "microbiome data", is data regarding the presence of, identity of, and measure of populations of microscopic organisms living in or on a user, including DNA and RNA, enzymes, peptides, biomarkers, toxins, and biologics originating from bacteria, viruses, fungi, protozoa, parasites, spores, eggs, or any other microbiological organisms that may be present in the body as resident flora, transient flora, pathogens, including opportunistic pathogens, or any other category of microbe. Various data that are represented by a microbiome analysis will be understood by those skilled in the art, after reviewing the disclosure in its entirety.

Continuing in referring to FIG. 1, plurality of dimensions of biological extraction 108 data of a user may include gut wall and food sensitivity analysis 140 that comes from at least a first user questionnaire analysis. As described here, "gut wall and food sensitivity," is data relating to a user's food intolerances, allergies, or any other sensitivities and/or adverse reaction to a food, supplement, beverage, or the like, including relations to gut wall strength and/or integrity of gastrointestinal epithelium, including condition of intestinal villi, adsorption kinetics of macro and micronutrients, immunological function, and any other data referring to the gastrointestinal tract, further including for instance, and without limitation, data as described in U.S. Nonprovisional application Ser. No. 16/530,329. In non-limiting examples, gut wall and food sensitivity analysis and associated data may originate from data generated by tests as referenced above and/or data from a first user questionnaire, database, medical professional, and/or subset of users, without limitation. It will be understood by those skilled in the art, after reviewing the disclosure in its entirety, the various data that are represented by a gut wall and food sensitivity analysis.

Continuing in referring to FIG. 1, plurality of dimensions of biological extraction 108 data of a user may include a genetic analysis 144 obtained from at least a user physical sample. As described here, "physical sample," is a biological user sample including blood, urine, feces, hair, saliva, skin, interstitial fluid, biopsy, or any other physical biological sample that genetic information can be obtained. As described here, "genetic analysis," refers to the analysis of any genetic material including nucleic acids such as DNA and RNA, which may correspond to genetic elements of a user including coding regions (genes), non-coding regions such as promoters, enhancers, transposons, genome-integrated viral DNA, and the presence of structural RNAs, such as tRNAs, miRNAs and other RNA types, and analysis thereof; analysis may refer to detecting the presence of, enumeration of, and/or determining the sequence of a nucleic acid and/or stretch of nucleic acid. Genetic analysis 144 data may be stored and/or retrieved from a database, as described below. It will be understood by those skilled in the art, after reviewing the disclosure in its entirety, the various data that are represented by a genetic analysis.

Continuing in referring to FIG. 1, plurality of dimensions of biological extraction 108 data of a user includes an epigenetic analysis 148; epigenetic analysis 148 may be obtained from at least a genetic analysis. As described here, "epigenetic analysis," is an analysis of genetic data including any mathematical, causative, correlated, proportional, heuristic, and/or any other relationship regarding the sequence of a nucleic acid and/or stretch of nucleic acid. Epigenetic analysis 148 data, as used herein, without limitation, may refer to identification and/or enumeration of single nucleotide polymorphisms (SNPs) in one or more genes and/or non-coding regions, relative numbers of expression of genes and/or non-coding regions, the identification and/or enumeration of the presence of mutations, including germ-line mutations and somatic mutations, and any other data that can be used for genotyping, inferring, calculating, determining, and/or any other analysis from at least an element of a genetic analysis. It will be understood by those skilled in the art, after reviewing the disclosure in its entirety, the various data that are represented by an epigenetic analysis.

Continuing in referring to FIG. 1, receiving plurality of dimensions of biological extraction 108 data of a user may include receiving a blood test 152 from at least a user sample of blood. A "blood test," as described herein, is a biochemical and/or clinical test administered with user blood sample as a material. Biological extraction data originating from a blood test 152 and/or a blood test 152 analysis may include biochemical and/or clinical chemistry data including without limitation, quantitative and/or qualitative information on the presence of enzyme content, such as liver enzymes including ALT and AST, blood proteins such as albumin, creatine kinase, hemoglobin, ferritin, metabolites such as glucose, triglycerides, LDL and HDL cholesterol, biomarkers such as for cancer, neurodegenerative disease, or diabetes, hormones such as insulin, cortisol, testosterone, estrogen, and progesterone, red blood cell viability and count, white blood cell viability and count, or any other data from a blood sample. It will be understood by those skilled in the art, after reviewing the disclosure in its entirety, the various data that are represented by a blood test 152 analysis.

Continuing in referring to FIG. 1, receiving plurality of dimensions of biological extraction 108 data of a user may include receiving a toxicity report 156. A "toxicity report," as described herein is at least an element of data describing the use of current medications, prescribed medications that are not currently taken, recreational drugs, tobacco products, alcohol, caffeine intake, topicals, supplements, drug allergies, hypersensitivities, immunological disorders, and/or any toxic or adverse effects of combinations of these and/or any other biologics, medications, supplements, beverages, foods, or any other chemical with a biological effect. User toxicity report 156 data may come from a variety of sources, including without limitation, a user questionnaire, medical professional input, or any other advocate on behalf a user such as a caretaker. It will be understood by those skilled in the art, after reviewing the disclosure in its entirety, the various data that are represented by a toxicity report 156.

Figure 2:
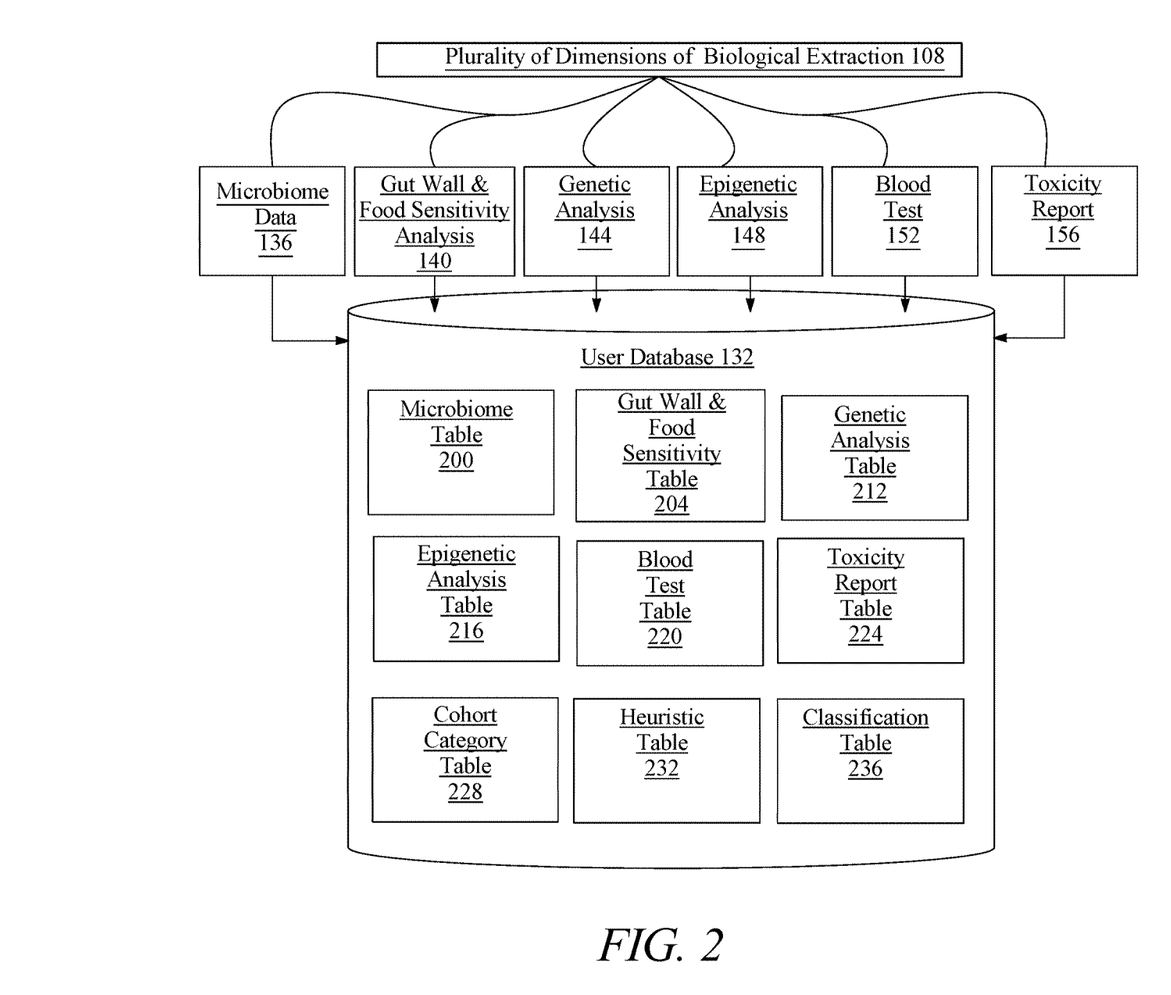
FIG. 2 is a block diagram of an exemplary embodiment of a user database.

Now referring to FIG. 2, the plurality of dimensions of biological extraction 108 data may be stored and/or retrieved by a computing device designed and configured to store and/or retrieve data from a user database 132. User database 132 may refer to a "database" which at least a computing device 104 may, as a non-limiting example, store and/or retrieve data from various tables as described below. Determinations by a machine learning process may also be stored and/or retrieved from the user database 132, for instance in non-limiting examples a correlated biosketch measurements 116. As a non-limiting example, user database may organize data according to one or more user database tables. One or more database tables may be linked to one another by, for instance in a non-limiting example, common column values. For instance, a common column between two tables of database may include an identifier of a submission, such as a form entry, textual submission, research paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which data from one or more tables may be linked and/or related to data in one or more other tables.

Still referring to FIG. 2, in a non-limiting embodiment, one or more user database tables of a user database 132 may include, as a non-limiting example, a microbiome table 200, which may include the identity of microbes present in a user sample for use in, without limitation, predicting and/or calculating a correlated biosketch measurement 116 as it relates to metabolism of a user and/or correlating a dimension of biological extraction data, entries indicating degrees of relevance to and/or efficacy in predicting metabolism of a user, and/or other elements of data computing device and/or system may use to determine usefulness and/or relevance of a plurality of dimensions of biological extraction 108 data in determining metabolism as described in this disclosure. One or more tables may include, without limitation, a gut wall and food sensitivity table 204, which may correlate biological extraction data and/or combinations thereof to one or more measures of food intolerances; gut wall and food sensitivity table may contain a plurality of entries associating at least an element of a dimension of biological extraction data with gut wall and food sensitivity. One or more tables may include, without limitation, a genetic analysis table 212, which may contain one or more inputs identifying one or more categories of data, for instance the DNA sequence of a metabolic gene. One or more tables may include, without limitation, an epigenetic analysis table 216, which may contain one or more inputs identifying one or more categories of data, for instance the genotypic differences among a subset of users. One or more tables may include, without limitation, a blood test table 220 which may contain one or more inputs identifying one or more categories of data, for instance white blood cell viability and count. One or more tables may include, without limitation, a toxicity report table 224, which may contain one or more inputs identifying one or more categories of data, for instance user consumption of alcohol over time. One or more tables may include, without limitation, a cohort category table 228 which may contain one or more inputs identifying one or more categories of data, for instance microbiome data, gut wall and food sensitivity data, genetic data, epigenetic data, blood test 152 data, and/or toxicity report data, with regard to which users having matching or similar data may be expected to have similar dimensional history 124 and/or biological outcome as a result of biosketch measurements and/or other biological extraction data. One or more tables may include, without limitation, a heuristic table 232, which may include one or more inputs describing potential mathematical relationships between at least an element of a plurality of dimensions of biological extraction 108 data, dimensional history 124, and/or biological outcome, as described in further detail below. One or more tables may include, without limitation, a classification table 236, which may include one or more inputs describing potential subsets of users and/or user data between at least an element of a dimension of biological extraction data, dimensional history 124, and/or biological outcome, by using a classifier, as described in further detail below.

Continuing in referring to FIG. 2, in a non-limiting embodiment, one or more user database tables of a user database 132 may include, as a non-limiting example, a classification table 236, which may include data that identifies a set of users having one or more features in common, based upon at least an element of a plurality of dimensions of biological extraction 108 data.

Referring again to FIG. 1, a set of users such as a set in classification table 236 may be identified and/or populated therein by a classifier and/or classification algorithm. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. User classifier may be configured to output identifiers of a bin and/or set of users identified as similar using classification algorithm 160, where a "identifier" is a datum that labels or otherwise identifies a user set; that is, a label identifying a set of users that have sets of user data, such as without limitation biological extractions, that are clustered together, found to be close under a distance metric as described below, or the like. A user set may be a collection of users having closely related user data regarding one or more categories for classification as described above. User classifier may include a classifier configured to input user data and output identifiers of user sets.

Further referring to FIG. 1, computing device and/or another device may generate user classifier using classification algorithm 160, defined as a process whereby a computing device derives a classifier from user classification training data 128. Classification algorithm may be trained by computing device and/or one or more other devices in or communicating with system using training data 128 containing a plurality of sets of data pertaining to a plurality of users. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Continuing in reference to FIG. 1, a classifier may indicate a subset of users mutually similar in at least one or more elements of data including a dimension of biological extraction data, dimensional history 124 data, biological outcome data, and/or any other available data, to match a user to a dimensional history 124 and/or biological outcome. Matching a user to a dimensional history 124 and/or biological outcome via a classifier may correspond to identifying any correlated biosketch measurements 116, as described in further detail below. A classifier may be an input to a machine learning process to calculate, modify, or otherwise generate dimensional history 124, and/or biological outcome information for a user. Classifiers generated from a classification algorithm 160 may be stored and/or retrieved in a user database 132, such as a cohort category table 228, for use by machine learning process 124, as described herein, including for instance, and without limitation, as described in U.S. Nonprovisional application Ser. No. 16/865,740, filed on May 4, 2020, and entitled "METHODS AND SYSTEMS FOR SYSTEM FOR NUTRITIONAL RECOMMENDATION 140 USING ARTIFICIAL INTELLIGENCE ANALYSIS FOR IMMUNE IMPACTS," the entirety of which is incorporated herein by reference.

Continuing in reference to FIG. 1, inputs and outputs of a machine learning model such as first machine-learning model 112 may be selected based on a user classifier, as described above. A classifier may be used to differentiate an explicit category of data as an input to a machine learning model based on a subset of useful data. Alternatively or additionally, a classifier may be assigned, as described before, to an explicit category or subset of data of an output of a machine learning model. For instance, different subsets of a first machine learning model output may contain data useful to subsequent machine learning models. A classifier for input and/or output of a machine learning model may be stored and/or retrieved by a computing device, without limitation, from a database.

Referring to FIG. 1, first machine learning model 112 may generate a dimensional history 124. First machine learning model 112 may input a plurality of dimensions of biological extraction 108 data, may and may generate a dimensional history 124 of a user. Alternatively or additionally, a dimensional history 124 may refer to an output from a machine learning process using a first machine learning model 112 summarizing values calculated from a plurality of correlated biosketch measurements 116. In non-limiting illustrative examples, a correlated biosketch measurement 116 may be a function, or vector, that describes a mathematical relationship between user's propensity to harbor a strain of bacteria in their microbiome that metabolizes a pharmaceutical compound described in a user's toxicity report 156. In further non-limiting illustrative examples, without limitation, this may be expressed, for instance, as a function describing the relationship for any values of microbiome data and/or any values of toxicity report data. In non-limiting illustrative examples, a dimensional history 124 output of a machine learning model may describe a corrected, or weighed, therapeutic dose range value, without limitation, in an updated toxicity report 156 reflecting the correlated biosketch measurements 116 and blood test data of the therapeutic metabolite. In non-limiting examples, a dimensional history 124 of a user may include a toxicity report 156 that is corrected, altered, or modified in any way by data describing, for instance without limitation, a relationship between microbiome data 136 that corresponds to data of a toxicity report 156 that infers new pharmacokinetics previously unknown from the original data. A first machine learning process 120 generating a correlated biosketch measurement 116 may use an input of data that is stored and/or retrieved from a user database 132 and/or may use data that pertains to a first user and/or any number of other users based upon a classifier, as described above.

Continuing in referring to FIG. 1, calculating a correlated biosketch measurement 116 using a first machine learning process 120 includes training a first machine learning process 120 using training data 128 including data entries corresponding to users in a user set. In non-limiting examples, a machine learning process may be trained with data pertaining to a classifier generated by a classification algorithm 160 to generate a machine learning model, as previously described, to narrow training set data to a useful cohort or similar users. Machine learning models 128 generated from classifiers may be used with a first machine learning process 120 and a plurality of dimensions of biological extraction 108 input data to output at least a correlated biosketch measurement 116. In non-limiting illustrative examples, a classifier describing a subset of users based on a bacterial strain identified in the microbiome data 136, may be used with a first machine learning process 120 and a plurality of dimensions of biological extraction data 108 as an input to generate an output of a correlated biosketch measurement 116 that describes a relationship between a first user's data and a subset of other users. In further non-limiting illustrative examples, such a correlated biosketch measurement 116 may further increase the accuracy of a dimensional history 124 and/or biological outcome weighed with such a correlated biosketch measurement 116. In non-limiting illustrative examples, a first correlated biosketch measurement 116 may be used as an input to train a machine learning process to output a second correlated biosketch measurements 116. At least a correlated biosketch measurement 116 and at least a classifier may by stored and/or retrieved from a database, as described before. Computing device 104 is configured to output as a function of a plurality of dimensions of biological extraction data and a first machine learning model a dimensional history of the user. A dimensional history of the user includes any of the dimensional histories as described above in more detail above.

Continuing in referring to FIG. 1, computing device is configured to determine a biological outcome 168 of a user; determination includes using a second machine learning process 168 and at least a dimensional history 124 of a user. Computing device 104 determines using a second machine-learning process and a dimensional history of a user at least a biological outcome associated with a user. A "biological outcome," as described herein, is a potential diagnosis, prognosis, explanation, course-of-action, or similar conclusion. A biological outcome may be determined from at least a first dimensional history 124 and at least a second element of data, wherein the second element of data is biological extraction data, database data, a classifier, and/or a second dimensional history 124. In non-limiting examples, biological extraction data, database data, a classifier, and/or a second dimensional history 124 may be available to a computing device via, without limitation, online repositories, user databases, research databases, medical databases, and the like, as previously described. In non-limiting examples, a second machine learning process 168 may use a machine learning model trained with training data from, without limitation, at least a classifier generated by a classification algorithm 160 to narrow down dimensional histories into more selective, useful subsets of data. Additionally or alternatively, a second machine learning process 168 may use a machine learning model trained with training data from, without limitation, a database. A second machine learning process 168 may be a supervised machine learning process, and/or any machine learning process suitable for a first machine learning process 120, as previously described. In non-limiting illustrative examples, a biological outcome 168 may be the output of a second machine learning process 168, for instance and without limitation, from an input of a dimensional history 124 and an input of an element of data from a database. In non-limiting illustrative examples, a biological outcome 168 may be an output that a user has a propensity for blood clots based on the dimensional history 124 describing the genetic analysis 144, epigenetic analysis 148, blood test 152 data, and toxicity report 156 data, wherein the biological outcome 168 output are values of probability of a variety of diagnoses involving blood clotting using a published criterion retrieved from a database. Biological outcome 168 outputs may be stored and/or retrieved from a database, as previously described. A first biological outcome 168 may be used as an input for a machine learning process, as previously described, to generate a second biological outcome 168. A first biological outcome 168 may be used as training data for a machine learning process, as previously described, to generate a machine learning model.

Continuing in referring to FIG. 1, determining a biological outcome 168 of a plurality of biological outcomes 168 of a user includes determining at least a long-term effect 172. A "long-term effect," as described herein, is the element of a biological outcome 168 that is a chronic, addressable or non-addressable, pathology, ailment, underlying affect, disorder, diagnosis, pattern, or any other biological outcome 168 that is calculated or otherwise determined from a dimensional history 124 of a user. In non-limiting illustrative examples, long-term effect 172 is the component output of a biological outcome 168 that may refer to diabetes, cancer, lacking a probiotic, or any other chronic biological outcome 168. In further non-limiting illustrative examples, a biological outcome 168 may include a long-term effect 172 output that describes the probability of a prognosis of deep vein thrombosis (DVT), heart attack, and/or stroke, based on the input of a dimensional history 124 of a user and the input of published criteria, such as the Wells' Criterion for determining DVT. In non-limiting illustrative embodiments, a machine learning process may be trained with training data 128 from a database and/or dimensional history 124, for instance without limitation, the Wells' Criterion for determining DVT, to generate a model for determining at least a long-term effect 172 of a biological outcome 168. In further non-limiting illustrative embodiments, a second machine learning process 168 outputting a biological outcome 168 may use an input of a dimensional history 124 and output an acute effect 176 describing the probability of a variety of potential diagnosis from that data, or likelihood that a person develops a disease in their lifetime. In further non-limiting examples, an acute effect 176 of a biological outcome 168 may be weighed for the presence of false-positives and false-negatives based upon correlated biosketch measurements 116 and/or classifiers to subsets of users that may share a suspected diagnosis or have confirmed a diagnosis. In further non-limiting examples, an acute effect 176 of a biological outcome 168 may describe no diagnosis or plan-of-action to be taken. This data may be stored and/or retrieved, without limitation, from a user database 128 or a source available to a computing device 104, as previously described. In non-limiting examples, an acute effect 176 of a biological outcome 168 may include an output predicting the likelihood of a disease, ailment, disorder, impairment, or the like, from the plurality of dimensions of biological extraction 108, and data available from online sources, and other databases 128. In further non-limiting illustrative examples, a biological outcome 168 may be output by a first machine learning model that is trained on data available from a database 128, user-reported data, and/or other sources of data available to computing device 104, to determine a probability of a long-term effect 172 and refine the accuracy of the determination.

Continuing in referring to FIG. 1, determining the at least a biological outcome 168 may include determining at least an acute effect 176 from at least a long-term effect 172. An "acute effect," as described herein, is a current plan devised to address at least a long-term effect 172 of a biological outcome 168. Acute effect 176 may be generated from a third machine learning process 178 with a long-term effect 172 and a second element of data, including a plurality of dimensions of biological extraction and/or data retrieved from a database. In non-limiting illustrative examples, a third machine learning process may take an input of a long-term effect describing the probability of stroke in a user and a list of preventative measures for strokes retrieved from a database, and output an acute effect 176 that describes potential immediate triggers for such strokes, and/or identifies such triggers as present in user based on plurality of dimensions of biological extractions; a user, another process and/or system, and/or a medical professional may use this to determine an appropriate course of action for a user matching the plurality of dimensions of biological extraction data that the long-term effect originated. In further non-limiting illustrative examples, a third machine learning process may take an input of a long-term effect 172 describing the possibility of a user's lactose intolerance and an element of a plurality of dimensions of biological extraction data that describes a user's microbiome to output an acute effect 176 describing a probiotic that is absent from a user's microbiome which may alleviate lactose intolerance. In non-limiting illustrative examples, a machine learning process may be trained using training data, which may be selected, without limitation, from training data pertaining to user and/or medical data matched to user using a classifier, a second long-term effect 172, a second biological outcome 168, and/or any data available to a computing device, as described above, to output a machine learning model for generating an acute effect 176. In non-limiting illustrative examples, an acute effect 176 of a biological outcome 168 may be an output of a recommended dietary restriction and/or dietary supplementation to resolve a long-term effect 172 based on a model trained with training data identified by a classifier describing a subset of users lacking the long-term effect 172. In further non-limiting examples, an acute effect 176 of a biological outcome 168 may describe no current deviation from a user's habits, lifestyle, of the like, regarding the long-term effect 172.

Figure 3:
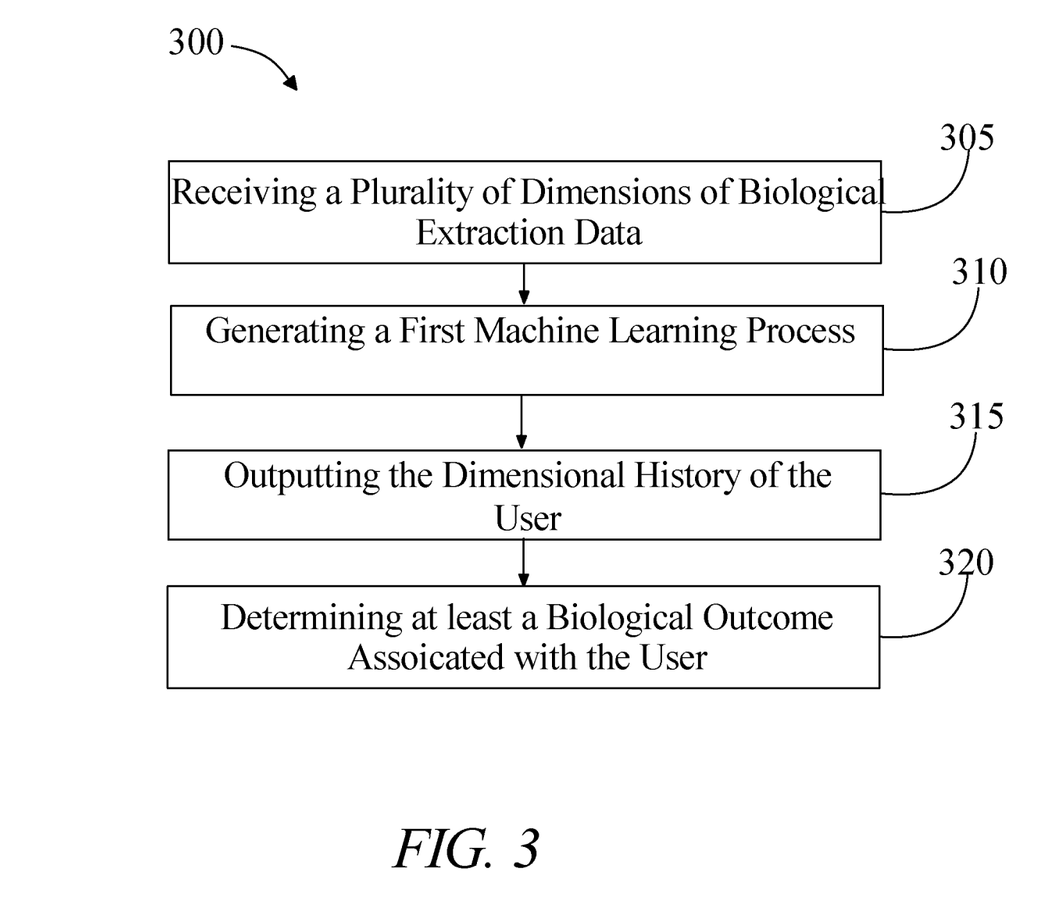
FIG. 3 is a flowchart describing a method using the system of the invention.

Referring now to FIG. 3, an exemplary embodiment of a method 300 of determining a plurality of biological outcomes 168 using plurality of dimensions of biological extraction 108 user data and artificial intelligence. At step 305, method 300 includes receiving by the at least a computing device 104, a plurality of dimensions of biological extraction data 108, including at least a microbiome data 136, at least a gut wall and food sensitivity analysis 144, at least a genetic analysis 144, at least an epigenetic analysis 148, at least a blood test 152, and at least a toxicity report 156; this may be implemented, without limitation, as described above in reference to FIGS. 1-2. At step 310, method 300 includes generating by the at least a computing device, using a first machine learning process, comprising a plurality of biosketch measurements wherein a first machine learning process is trained as a function of training data to output a dimensional history of a user as a function of biological extraction data. At step 315, computing device 104 outputs as a function of a plurality of dimensions of biological extraction data and a first machine-learning process, a dimensional history of a user. This may be performed utilizing any of the methodologies as described above in more detail in reference to FIG. 1. At step 320, method 300 includes determining, by the at least a computing device, using a second machine learning process 168 and at least a dimensional history 124, at least a biological outcome associated with a user, this may be implemented, without limitation, as described above in reference to FIGS. 1-2. It will be understood by those skilled in the art, after reviewing the disclosure in its entirety, the various ways data may be input in a computing device 104 and the various ways outputs may be displayed by a computing device 104 to a user for all steps described above.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 4:
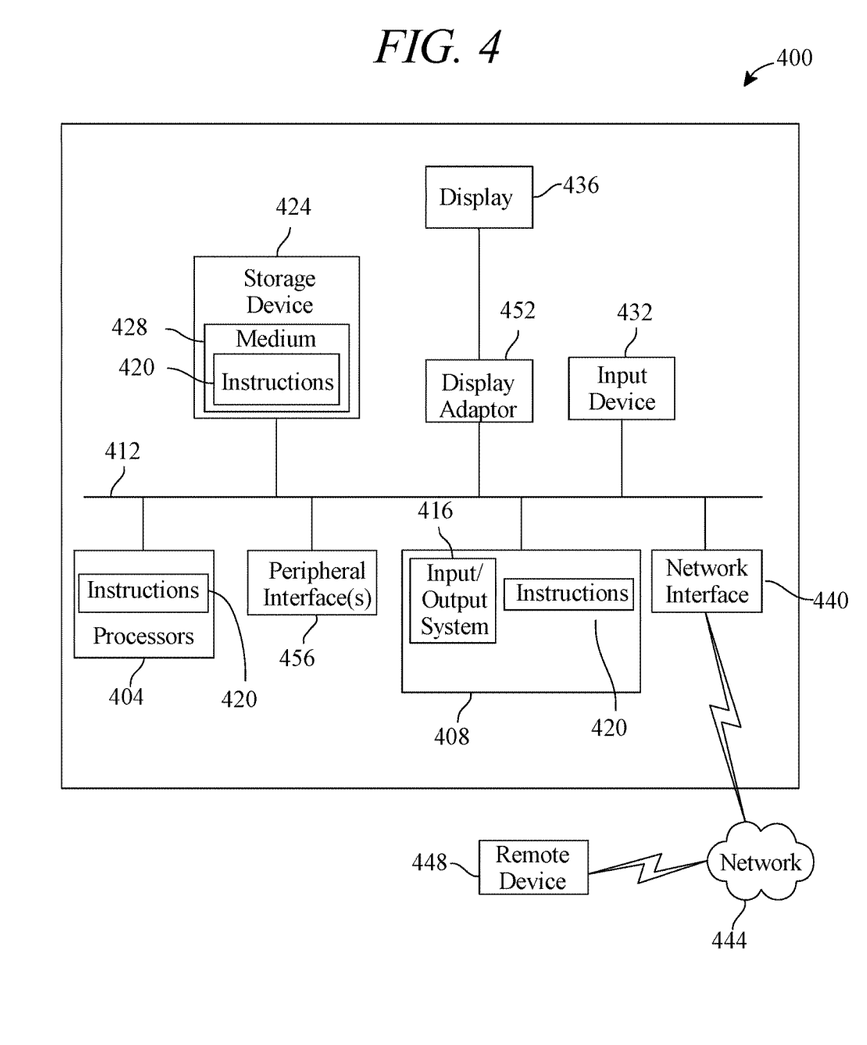
FIG. 4 is a block diagram of a computing system that can be used to implement any one or more of the methodologies disclosed herein and any one or more portions thereof.

FIG. 4 shows a diagrammatic representation of one embodiment of a computing device in the exemplary form of a computer system 400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 400 includes a processor 404 and a memory 408 that communicate with each other, and with other components, via a bus 412. Bus 412 may include any of several types of bus structures including, but not limited to, a memory bus, a memory controller, a peripheral bus, a local bus, and any combinations thereof, using any of a variety of bus architectures.

Processor 404 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 404 may be organized according to Von Neumann and/or Harvard architecture as a non-limiting example. Processor 404 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 408 may include various components (e.g., machine-readable media) including, but not limited to, a random-access memory component, a read only component, and any combinations thereof. In one example, a basic input/output system 416 (BIOS), including basic routines that help to transfer information between elements within computer system 400, such as during start-up, may be stored in memory 408. Memory 408 may also include (e.g., stored on one or more machine-readable media) instructions (e.g., software) 420 embodying any one or more of the aspects and/or methodologies of the present disclosure. In another example, memory 408 may further include any number of program modules including, but not limited to, an operating system, one or more application programs, other program modules, program data, and any combinations thereof.

Computer system 400 may also include a storage device 424. Examples of a storage device (e.g., storage device 424) include, but are not limited to, a hard disk drive, a magnetic disk drive, an optical disc drive in combination with an optical medium, a solid-state memory device, and any combinations thereof. Storage device 424 may be connected to bus 412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 424 (or one or more components thereof) may be removably interfaced with computer system 400 (e.g., via an external port connector (not shown)). Particularly, storage device 424 and an associated machine-readable medium 428 may provide nonvolatile and/or volatile storage of machine-readable instructions, data structures, program modules, and/or other data for computer system 400. In one example, software 420 may reside, completely or partially, within machine-readable medium 428. In another example, software 420 may reside, completely or partially, within processor 404.

Computer system 400 may also include an input device 432. In one example, a user of computer system 400 may enter commands and/or other information into computer system 400 via input device 432. Examples of an input device 432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 432 may be interfaced to bus 412 via any of a variety of interfaces (not shown) including, but not limited to, a serial interface, a parallel interface, a game port, a USB interface, a FIREWIRE interface, a direct interface to bus 412, and any combinations thereof. Input device 432 may include a touch screen interface that may be a part of or separate from display 436, discussed further below. Input device 432 may be utilized as a user selection device for selecting one or more graphical representations in a graphical interface as described above.

A user may also input commands and/or other information to computer system 400 via storage device 424 (e.g., a removable disk drive, a flash drive, etc.) and/or network interface device 440. A network interface device, such as network interface device 440, may be utilized for connecting computer system 400 to one or more of a variety of networks, such as network 444, and one or more remote devices 448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 444, may employ a wired and/or a wireless mode of communication. In general, any network topology may be used. Information (e.g., data, software 420, etc.) may be communicated to and/or from computer system 400 via network interface device 440.

Computer system 400 may further include a video display adapter 452 for communicating a displayable image to a display device, such as display device 436. Examples of a display device include, but are not limited to, a liquid crystal display (LCD), a cathode ray tube (CRT), a plasma display, a light emitting diode (LED) display, and any combinations thereof. Display adapter 452 and display device 436 may be utilized in combination with processor 404 to provide graphical representations of aspects of the present disclosure. In addition to a display device, computer system 400 may include one or more other peripheral output devices including, but not limited to, an audio speaker, a printer, and any combinations thereof. Such peripheral output devices may be connected to bus 412 via a peripheral interface 456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for determining a plurality of biological outcomes using a plurality of dimensions of biological extraction user data and artificial intelligence, the system comprising a computing device, wherein the computing device is designed and configured to:
   receive, a plurality of dimensions of biological extraction data, wherein receiving the plurality of dimensions of biological extraction comprises receiving at least a gut wall and food sensitivity analysis, wherein the at least a gut wall and food sensitivity analysis comprises data relating to a food intolerance of a user;
   generate a classifier, wherein the classifier identifies a subset of users mutually similar in the plurality of dimensions of biological extraction data;
   generate a first machine learning process comprising a plurality of correlated biosketch measurements, wherein each correlated biosketch measurement comprises a mathematical relationship between at least two elements of dimensional biological data, wherein generating the first machine learning process comprises training the first machine learning process as a function of training data to produce the plurality of correlated biosketch measurements and wherein the trained first machine learning process is configured to receive the plurality of dimensions of biological extraction data as an input and to output a dimensional history of the user as a function of biological extraction data and the plurality of correlated biosketch measurements; and
   determine, using a second machine learning process and the dimensional history of the user, at least a biological outcome associated with the user, wherein determining the at least a biological outcome comprises:
      determining a long-term effect as a function of the biological outcome associated with the user, wherein the long-term effect comprises a probability of a chronic element of the at least a biological outcome; and
      generating at least an acute effect using a third machine learning process, wherein the third machine learning process receives the long-term effect and the plurality of dimensions of biological extraction as inputs and outputs the at least an acute effect, wherein the at least an acute effect comprises descriptions of potential immediate triggers for the long-term effect.

2. The system of claim 1, wherein receiving the plurality of dimensions of biological extraction further comprises receiving data including at least a microbiome datum, at least a genetic analysis, at least an epigenetic analysis, at least a blood test, and at least a toxicity report.

3. The system of claim 2, wherein the microbiome datum includes microbiome analysis that comes from a user stool sample analysis.

4. The system of claim 1, wherein receiving the at least a gut wall and food sensitivity analysis further comprises receiving at least a gut wall and food sensitivity test including data on gut wall strength of the user.

5. The system of claim 2, wherein at least a genetic analysis is obtained from at least a user physical sample.

6. The system of claim 2, wherein the epigenetic analysis is obtained from the at least a genetic analysis.

7. The system of claim 1, wherein the classifier is stored in a user database and wherein the classifier is retrieved from a user database.

8. The system of claim 2, wherein receiving the plurality of dimensions of biological extraction data of a user further comprises receiving a toxicity report.

9. The system of claim 1 further comprising:
   identifying, using a classifier, a plurality of training data entries corresponding to the user; and
   training the first machine learning process further as a function of the plurality of training data entries.

10. A method of determining a plurality of biological outcomes using a plurality of dimensions of biological extraction user data and artificial intelligence, the method comprising:

receiving by at least a computing device, a plurality of dimensions of biological extraction data, wherein receiving the plurality of dimensions of biological extraction comprises receiving at least a gut wall and food sensitivity analysis, wherein the at least a gut wall and food sensitivity analysis comprises data relating to a food intolerance of a user;

generating a classifier, wherein the classifier identifies a subset of users mutually similar in the plurality of dimensions of biological extraction data;

generating, by the at least a computing device, a first machine-learning process comprising a plurality of correlated biosketch measurements, wherein each correlated biosketch measurement comprises a mathematical relationship between at least two elements of dimensional biological data, wherein generating the first machine learning process comprises training the first machine learning process as a function of training data to produce the plurality of correlated biosketch measurements and wherein the trained first machine learning process is configured to receive the plurality of dimensions of biological extraction data as an input and to output a dimensional history of the user as a function of biological extraction data and the plurality of correlated biosketch measurements; and determining, by the at least a computing device, using a second machine learning process and the dimensional history of the user, at least a biological outcome associated with the user, wherein determining the at least a biological outcome comprises:

determining a long-term effect as a function of the biological outcome associated with the user, wherein the long-term effect comprises a probability of a chronic element of the at least a biological outcome; and generating at least an acute effect using a third machine learning process, wherein the third machine learning process receives the long-term effect and the plurality of dimensions of biological extraction as inputs and outputs the at least an acute effect, wherein the at least an acute effect comprises descriptions of potential immediate triggers for the long-term effect.

11. The method of claim 10, wherein receiving plurality of dimensions of biological extraction of user data further comprises data including at least a microbiome datum, at least a genetic analysis, at least an epigenetic analysis, at least a blood test, and at least a toxicity report.

12. The method of claim 10, wherein generating a dimensional history of a user further comprises inferring the dimensional history, using the first machine learning process, from the plurality of dimensions of biological extraction data.

13. The method of claim 12, further comprising:
calculating a correlated biosketch measurement; and
weighting the plurality of dimensions of biological extraction data with the correlated biosketch measurement.

14. The method of claim 13, wherein calculating a correlated biosketch measurement further comprises using the first machine learning process and data including plurality of dimensions of biological extraction data.

15. The method of claim 10, wherein determining a biological outcome further comprises using the second machine learning process, wherein the second machine learning process is trained using training data including at least the dimensional history.

16. The system of claim 2, wherein receiving the plurality of dimensions of biological extraction data of a user further comprises receiving a saliva sample from the user.

* * * * *